United States Patent
McKay et al.

(10) Patent No.: US 11,009,577 B2
(45) Date of Patent: May 18, 2021

(54) SYSTEM AND METHOD FOR NYQUIST GHOST CORRECTION IN MEDICAL IMAGING

(71) Applicant: REGENTS OF THE UNIVERSITY OF MINNESOTA, Minneapolis, MN (US)

(72) Inventors: Jessica McKay, Minneapolis, MN (US); Patrick Bolan, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/430,110

(22) Filed: Jun. 3, 2019

(65) Prior Publication Data

US 2019/0369192 A1 Dec. 5, 2019

Related U.S. Application Data

(60) Provisional application No. 62/679,110, filed on Jun. 1, 2018.

(51) Int. Cl.
| | | |
|---|---|---|
| *G01R 33/561* | (2006.01) | |
| *A61B 5/055* | (2006.01) | |
| *G01R 33/565* | (2006.01) | |
| *G01R 33/48* | (2006.01) | |
| *G16H 30/40* | (2018.01) | |

(52) U.S. Cl.
CPC .......... *G01R 33/5611* (2013.01); *A61B 5/055* (2013.01); *G01R 33/4818* (2013.01); *G01R 33/56554* (2013.01); *G06T 2207/10088* (2013.01); *G16H 30/40* (2018.01)

(58) Field of Classification Search
CPC .......... G01R 33/5611; G01R 33/56554; G01R 33/4818; G01R 33/56545; G01R 33/4835; G06T 2207/10088; G16H 30/40; G16H 50/50; G16H 30/20; A61B 5/055; A61B 5/7203

See application file for complete search history.

(56) References Cited

U.S. PATENT DOCUMENTS

| | | | |
|---|---|---|---|
| 5,151,656 A | 9/1992 | Maier | |
| 5,581,184 A | 12/1996 | Heid | |
| 5,672,969 A | 9/1997 | Zhou | |
| 6,043,651 A | 3/2000 | Heid | |

(Continued)

OTHER PUBLICATIONS

Atkinson, D., et al. "Automatic compensation of motion artifacts in MRI." Magnetic Resonance in Medicine: An official Journal of the International Society for Magnetic Resonance in Medicine 41.1 (1999): 163-170.

(Continued)

*Primary Examiner* — Susan S Lee
(74) *Attorney, Agent, or Firm* — Quarles & Brady LLP

(57) ABSTRACT

A system and computerized method for generating magnetic resonance imaging (MRI) images is provided that includes accessing data acquired from a subject using an MRI system that includes Nyquist ghosts and processing the data using a cost function that exploits a cosine and sine modulation in a ghosted image component of the data. An image of the subject is produced from the data after processing the data using the cost function.

20 Claims, 9 Drawing Sheets
(5 of 9 Drawing Sheet(s) Filed in Color)

(56) References Cited

U.S. PATENT DOCUMENTS

| | | | |
|---|---|---|---|
| 6,100,689 | A | 8/2000 | Huff |
| 6,259,250 | B1 | 7/2001 | Mock |
| 7,403,002 | B2 | 7/2008 | Feiweier |
| 7,772,847 | B2 | 8/2010 | Zur |
| 8,483,457 | B2 | 7/2013 | Hinks |
| 10,274,569 | B2 | 4/2019 | Chen |
| 2008/0292167 | A1* | 11/2008 | Todd .................. G01R 33/4804 382/131 |
| 2016/0041248 | A1 | 2/2016 | Chen |

OTHER PUBLICATIONS

Bruder, H., et al. "Image reconstruction for echo planar imaging with nonequidistant k-space sampling." Magnetic Resonance in Medicine 23.2 (1992): 311-323.

Buonocore, M.H., et al. "High spatial resolution EPI using an odd number of interleaves." Magnetic Resonance in Medicine: An Official Journal of the International Society for Magnetic Resonance in Medicine 41.6 (1999): 1199-1205.

Buonocore, M.H., et al. (2001). Image-based ghost correction for interleaved EPI. Magnetic Resonance in Medicine 45, 96-108.

Buonocore, M.H., et al. Ghost Artifact Reduction for Echo Planar Imaging Using Image Phase Correction. Magn. Reson. Med. 1997;38:89-100.

Chen, N., et al. (2004). Removal of EPI Nyquist ghost artifacts with two-dimensional phase correction. Magnetic Resonance in Medicine 51, 1247-1253.

Chen, N.-K., et al. (2011). Two-dimensional phase cycled reconstruction for inherent correction of echo-planar Imaging nyquist artifacts. Magnetic Resonance in Medicine 66, 1057-1066.

Clare, S. "Iterative Nyquist ghost correction for single and multi-shot EPI using an entropy measure." Proc 11th Annual Meeting ISMRM, Toronto. 2003.

Clare, S., et al. "Ghost artefact in fMRI: comparison of techniques for reducing the N/2 ghost." Proceedings of the ISMRM, on CD-ROM. 1998.

Constable, R. T., et al. "Why MEM does not work in MR image reconstruction." Magnetic resonance in medicine 14.1 (1990): 12-25.

Feinberg DA, et al. Multiplexed Echo Planar Imaging for Sub-Second Whole Brain FMRI and Fast Diffusion Imaging Valdes-Sosa PA, editor. PLoS One 2010;5:e15710.

Foxall DL, et al. Rapid iterative reconstruction for echo planar imaging. Magn. Reson. Med. 1999;42:541-547.

Griswold MA, et al. Generalized autocalibrating partially parallel acquisitions (GRAPPA). Magn. Reson. Med. 2002;47:1202-1210.

Hoge WS, et al. (2016). Dual-polarity GRAPPA for simultaneous reconstruction and ghost correction of echo planar imaging data: Dual-Polarity GRAPPA for EPI. Magnetic Resonance in Medicine 76, 32-44.

Hoge WS, et al. Robust EPI Nyquist ghost elimination via spatial and temporal encoding. Magn. Reson. Med. 2010;64:1781-1791.

Hu X, et al. Artifact reduction in EPI with phase-encoded reference scan. Magn. Reson. Med. Off. J. Soc. Magn. Reson. Med. Soc. Magn. Reson. Med. 1996;36:166-171.

Hylton N, et al. ACRIN 6698 Diffusion Weighted MR Imaging Biomarkers for Assessment of Breast Cancer Response to Neoadjuvant Treatment: A sub-study of the I-SPY 2 TRIAL. Am. Coll. Radiol. Imaging Netw. 2012.

Kellman, P., et al. (2006). Phased array ghost elimination. NMR in Biomedicine 19, 352-361.

Larkman DJ, et al. Use of multicoil arrays for separation of signal from multiple slices simultaneously excited. J. Magn. Reson. Imaging 2001;13:313-317.

Lee J, et al. Reference-free single-pass EPI Nyquist ghost correction using annihilating filter-based low rank Hankel matrix (ALOHA): Reference-Free Single-Pass EPI Nyquist Ghost Correction using ALOHA. Magn. Reson. Med. 2016.

Lee, K.J., et al. (2002). Image-based EPI ghost correction using an algorithm based on projection onto convex sets (POCS). Magnetic Resonance in Medicine 47, 812-817.

Mani M, et al. Comprehensive reconstruction of multi-shot multi-channel diffusion data using Mussels. In: Engineering in Medicine and Biology Society (EMBC), 2016 IEEE 38th Annual International Conference of the. IEEE; 2016. pp. 1107-1110.

McKay JA, et al. Comparison of Referenceless Methods for EPI Ghost Correction in Breast Diffusion Weighted maging. MRM. Published Jun. 1, 2018.

Mckay JA, et al. Novel Image-based Nyquist Ghost Correction of Diffusion-Weighted Echo Planar Imaging using Shost/Object Minimization. MRM. Published Jun. 1, 2018.

Moeller S, et al. Multiband multislice GE-EPI at 7 tesla, with 16-fold acceleration using partial parallel imaging with application to high spatial and temporal whole-brain fMRI. Magn. Reson. Med. 2010;63:1144-1153.

Peterson, E., et al. (2015). Acquisition-free Nyquist ghost correction for parallel imaging accelerated EPI. In Proc. Intl. Soc. Mag. Reson. Med., (Toronto, Ontario), p. 0075.

Setsompop K, et al. Blipped-controlled aliasing in parallel imaging for simultaneous multislice echo planar imaging with reduced gfactor penalty. Magn. Reson. Med. 2012;67:1210-1224.

Shannon. "A mathematical theory of communication." The Bell system technical journal 27.3 (1948): 379-423.

Skare, S., et al. (2006). A fast and robust minimum entropy based non-interactive Nyquist ghost correction algorithm. In Proc. Intl. Soc. Mag. Reson. Med, (Seattle, Washington), p. 2349.

Smith, S. M. "Fast robust automated brain extraction." Human brain mapping 17.3 (2002): 143-155.

Sotiropoulos et al. "Advances in diffusion MRI acquisition and processing in the Human Connectome Project." Neuroimage 80 (2013): 125-143.

Xiang, Q.-S., et al. (2007). Correction for geometric distortion and N/2 ghosting in EPI by phase labeling for additional mordinate encoding (PLACE). Magnetic Resonance in Medicine 57, 731-741.

Xu, D., et al. (2010). Robust 2D phase correction for echo planar imaging under a tight field-of-view. Magnetic Resonance in Medicine 64, 1800-1813.

Zhang, Y., et al. (2004). Reference-scan-free method for automated correction of nyquist ghost artifacts in achoplanar brain images. Magnetic Resonance in Medicine 51, 621-624.

* cited by examiner

FIG. 4A
b = 0 s/mm² DWI
FIG. 4B
T₁-weighted anatomical
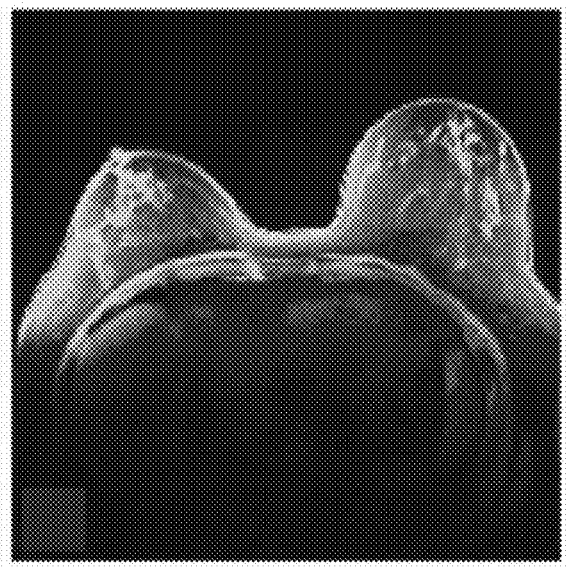
Object Mask
Background Signal
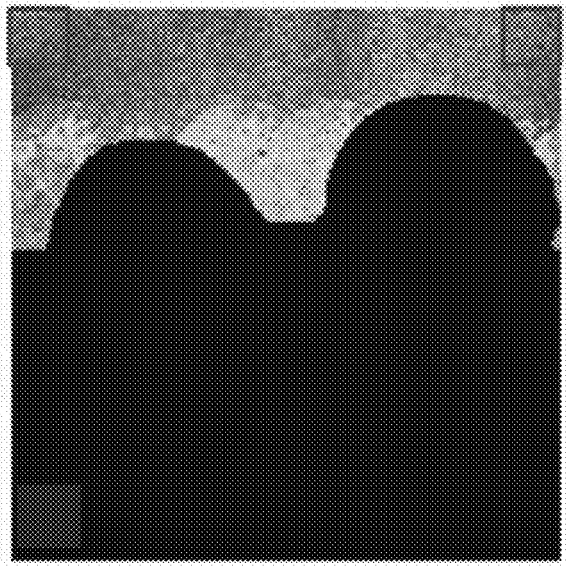
FIG. 4C
FIG. 4D

SYSTEM AND METHOD FOR NYQUIST GHOST CORRECTION IN MEDICAL IMAGING

CROSS REFERENCE TO RELATED APPLICATIONS

This application is based on, claims priority to, and incorporates herein by reference in its entirety, U.S. Provisional Application Ser. No. 62/679,110, filed Jun. 1, 2018, and entitled "System and Method for Nyquist Ghost Correction in Medical Imaging."

STATEMENT REGARDING FEDERALLY-SPONSORED RESEARCH

This invention was made with government support under OD017974. EB015894 and CA201834 awarded by National Institutes of Health. The government has certain rights in the invention.

BACKGROUND

The present disclosure relates to systems and methods for producing medical images. More particularly, the present disclosure relates to systems and methods for producing improved images with reduced Nyquist ghosting using magnetic resonance imaging (MRI) systems.

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment Mz is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, Mz, may be rotated, or "tipped" into the x-y plane to produce a net transverse magnetic moment Mt, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance (NMR) phenomenon is exploited.

When utilizing these signals to produce images, magnetic field gradients (Gx, Gy, and Gz) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

"Spin echoes" are produced in MRI when employing multiple RF pulses, typically at least an excitation RF pulse and a single refocusing RF pulse. In a spin echo (SE) pulse sequences, the flip angles for these pulses are often 90° and 180°, respectively. A spin echo, formed by the refocusing RF pulse, is typically encoded as a single k-space line beginning at a time from the RF pulse until acquisition, which defines an echo time (TE). This combination of pulses and echo acquisitions is repeated to define a repetition time (TR) until all desired lines of k-space are acquired. SE pulse sequences are often employed for a variety of clinical applications, for example, because the SE pulse sequence can be used for a variety of contrast weightings, including T1-, T2-, proton density-, or diffusion-weighting.

Diffusion-weighted imaging (DWI) is often performed using the SE, echo-planar imaging (EPI) pulse sequence. For some applications, such as breast imaging, a single-shot (SS), SS EPI pulse sequence may be employed. Regardless of the particular pulse sequence employed, due to the alternating nature of EPI readout (RO) lines, eddy currents, imperfect gradients, and timing errors can cause inconsistencies between k-space lines of opposite polarity (RO+/RO−), which manifest as Nyquist, or N/2, ghosts.

Nyquist ghosts are often corrected by acquiring a three-line navigator to measure the difference between alternating RO lines, which is modeled as a linear phase error. While the three-line navigator generally performs well for brain imaging, it often fails in body imaging due to insufficient fat suppression and increased B0 inhomogeneity. As such, several other ghost correction methods have been proposed including a full-phase navigator, 2D phase-mapping approaches, acceleration-based techniques, methods that enforce low-rank structure of multi-channel data, and a class of methods, termed referenceless methods, that use the EPI data for self-correction.

Some examples of referenceless methods include Lee J, Jin K H, Ye J C. Reference-free single-pass EPI Nyquist ghost correction using annihilating filter-based low rank Hankel matrix (ALOHA): Reference-Free Single-Pass EPI Nyquist Ghost Correction using ALOHA. Magn. Reson. Med. 2016:n/a-n/a. doi:10.1002/mrm.26077; Published US Patent Application 2016/0041248; Clare S. Iterative Nyquist ghost correction for single and multi-shot EPI using an entropy measure. In: Proceedings of the 16th annual meeting of ISMRM, Toronto, Canada; 2003. p.1041; Peterson E, Aksoy M, Maclaren J, Bammer R. Acquisition-free Nyquist ghost correction for parallel imaging accelerated EPI. In: Proc. Intl. Soc. Mag. Reson. Med. Vol. 23. Toronto, Ontario; 2015. p. 75; 17. Foxall D L, Harvey P R, Huang J. Rapid iterative reconstruction for echo planar imaging. Magn. Reson. Med. 1999; 42:541-547. doi: 10.1002/(SICI)1522-2594(199909)42:3<541::AIDMRM16>3.0.CO;2-F; 18. Lee K J, Barber D C, Paley M N, Wilkinson I D, Papadakis N G, Griffiths P D. Image-based EPI ghost correction using an algorithm based on projection onto convex sets (POCS). Magn. Reson. Med. 2002; 47:812-817. doi: 10.1002/mrm.10101; and Skare S, Clayton D B, Newbould R, Moseley M, Bammer R. A fast and robust minimum entropy based non-interactive Nyquist ghost correction algorithm. In: Proc. Intl. Soc. Mag. Reson. Med. Vol. 14. Seattle, Wash.; 2006. p. 2349. Each of these is incorporated herein by reference.

These referenceless methods work by defining a cost function that is minimized when the data is ghost-free. One such method, which can be termed the "entropy method" uses the image entropy after a 2D Fourier transform as a heuristic cost function. Another method that can be referred to as the "SVD method," defines a cost function based on a singular value decomposition of k-space after rearranging into GRAPPA-like (generalized autocalibrating partial parallel acquisition) kernels.

Referenceless methods may be advantageous because they do not require the acquisition of any additional navigator or reference data, potentially allowing for decreased acquisition time and/or shortened TE, and easy integration with a wide range of acquisition strategies, including retrospective data. Because these techniques do not rely on coil sensitivity profiles, they should be suitable for combination with acceleration techniques, like in-plane parallel imaging (PI) and simultaneous multi-slice (SMS) acquisition techniques. Additionally, because they are data-driven, they may be limited by the low SNR of high b-values and high resolution DWI.

Thus, there is a need for systems and methods that allow for the acquisition of images (for example, DWI images) within the constraints of clinical imaging, for example, outside of the head, but without limiting the utility of such images due to Nyquist ghosting.

SUMMARY

The present disclosure overcomes the aforementioned drawbacks by providing systems and methods for self-correction of images, including diffusion weighted imaging (DWI), in combination with parallel imaging (PI) or multi-band/simultaneous multi-slice (SMS) imaging techniques. Thus, the present disclosure provides an approach to referenceless Nyquist ghost correction that overcomes the limitations of prior techniques and extends the clinical applicability of imaging techniques that have been previously evaluated to be of limited clinical use due to such ghosting.

In accordance with one aspect of the disclosure, a computerized method is provided for generating magnetic resonance imaging (MRI) images. The computerized method includes steps of at least (i) accessing data acquired from a subject using an MRI system that includes Nyquist ghosts and (ii) processing the data to control artifacts using a cost function that exploits a cosine and sine modulation in a ghosted image component of the data. The computerized method also includes (iii) displaying an image of the subject produced from the data after processing of step (ii).

In accordance with another aspect of the disclosure, a computerized method is provided for generating magnetic resonance imaging (MRI) images. The computerized method includes steps of at least (i) accessing data acquired from a subject using an MRI system that includes Nyquist ghosts and (ii) processing the data using multiple referenceless methods to produce combined data from the multiple referenceless methods. The computerized method further includes (iii) displaying an image of the subject produced from the combined data after processing of step (ii).

In accordance with yet another aspect of the disclosure, a computerized method is provided for generating magnetic resonance imaging (MRI) images. The computerized method includes steps of at least (i) accessing undersampled data acquired from a subject using an MRI system that includes Nyquist ghosts and (ii) processing the data using a referenceless method to reduce the Nyquist ghosts by using a cost function that exploits a cosine and sine modulation in a ghosted image component of the undersampled data. The computerized method further includes (iii) displaying an image of the subject produced from the undersampled data after processing of step (ii).

In accordance with a further aspect of the disclosure, a system is provided that includes a magnet system configured to generate a polarizing magnetic field about at least a portion of a subject and a magnetic gradient system including a plurality of magnetic gradient coils configured to apply at least one magnetic gradient field to the polarizing magnetic field. The system further includes a radio frequency (RF) system configured to apply an RF field to the subject and to receive magnetic resonance signals from the subject using a coil array and a computer system. The computer system is programmed to acquire imaging data acquired from a subject that includes Nyquist ghosts, wherein the imaging data was acquired using the MRI system and process the imaging data using a cost function to control the Nyquist ghosts in an image of the subject. The system includes a display configured to display the image of the subject produced from the data after processing the image data to control Nyquist ghosts.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or patent application file contains at least one drawing in color. Copies of this patent or patent application publication with color drawings will be provided by the Office upon request and payment of the necessary fee.

FIG. 4A is an image illustrating a measurement of ghost levels, such that Nyquist ghosts in a b=0 s/mm2 image can be seen in the background region between the breasts.

FIG. 4B is a T1-weigthed anatomical image.

FIG. 4C is an image created using the T1-weighted anatomical image of FIG. 4B to create an object mask, which is applied to the b=0 s/mm2 image of FIG. 4A.

FIG. 4D is an image showing the signal in the background region, which reflects the intensity of the residual ghost.

DETAILED DESCRIPTION

Figure 1:
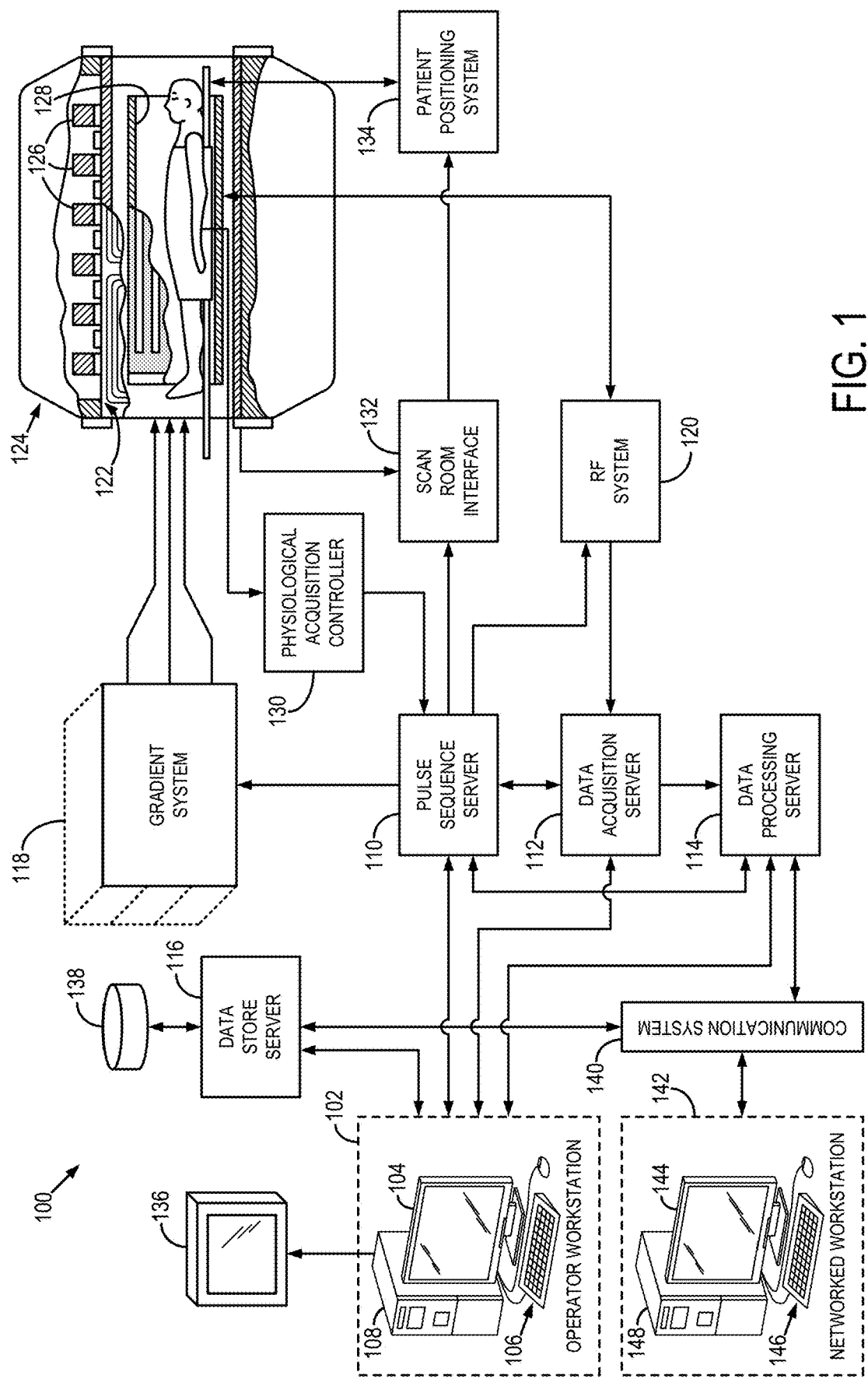
FIG. 1 is a block diagram of an example of a magnetic resonance imaging (MRI) system configured to employ the present disclosure.

Before turning to specific examples of the techniques in accordance with the present disclosure, it is noted that the techniques described herein may be implemented using any of a variety of magnetic resonance imaging (MRI) systems. Referring particularly to FIG. 1, an example of an MRI system 100 is illustrated. The MRI system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 may be connected to four servers: a pulse sequence server 110; a data acquisition server 112; a data processing server 114; and a data store server 116. These servers may be virtual or physical. The workstation 102 and each server 110, 112, 114, and 116 are connected to communicate with each other.

The pulse sequence server 110 functions in response to instructions downloaded from the workstation 102 to operate a gradient system 118 and a radiofrequency (RF) system 120. Gradient waveforms necessary to perform the prescribed scan are produced and applied to the gradient system 118, which excites gradient coils in an assembly 122 to produce the magnetic field gradients q, G, and q used for position encoding MR signals. The gradient coil assembly 122 forms part of a magnet assembly 124 that includes a polarizing magnet 126 and a whole-body RF coil 128 or a local coil.

RF excitation waveforms are applied to the RF coil 128, or a separate local coil, such as a head coil, by the RF system 120 to perform the prescribed magnetic resonance pulse sequence. Responsive MR signals detected by the RF coil 128, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF preamplifier that amplifies the MR signal received by the coil 128 to which it is connected, and a detector that detects and digitizes the quadrature components of the received MR signal. The magnitude of the received MR signal may thus be determined at any sampled point by the square root of the sum of the squares of the I and Q components:

$$M=\sqrt{I^2 \pm Q^2}$$ Eqn. 1;

and the phase of the received MR signal may also be determined:

$$\varphi = \tan^{-1}\left(\frac{Q}{I}\right).$$ Eqn. 2

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Images may be displayed on the operator display 104 or a display 136 that is located near the magnet assembly 124 for use by attending physicians or other clinicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communication system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100.

Figure 2A:
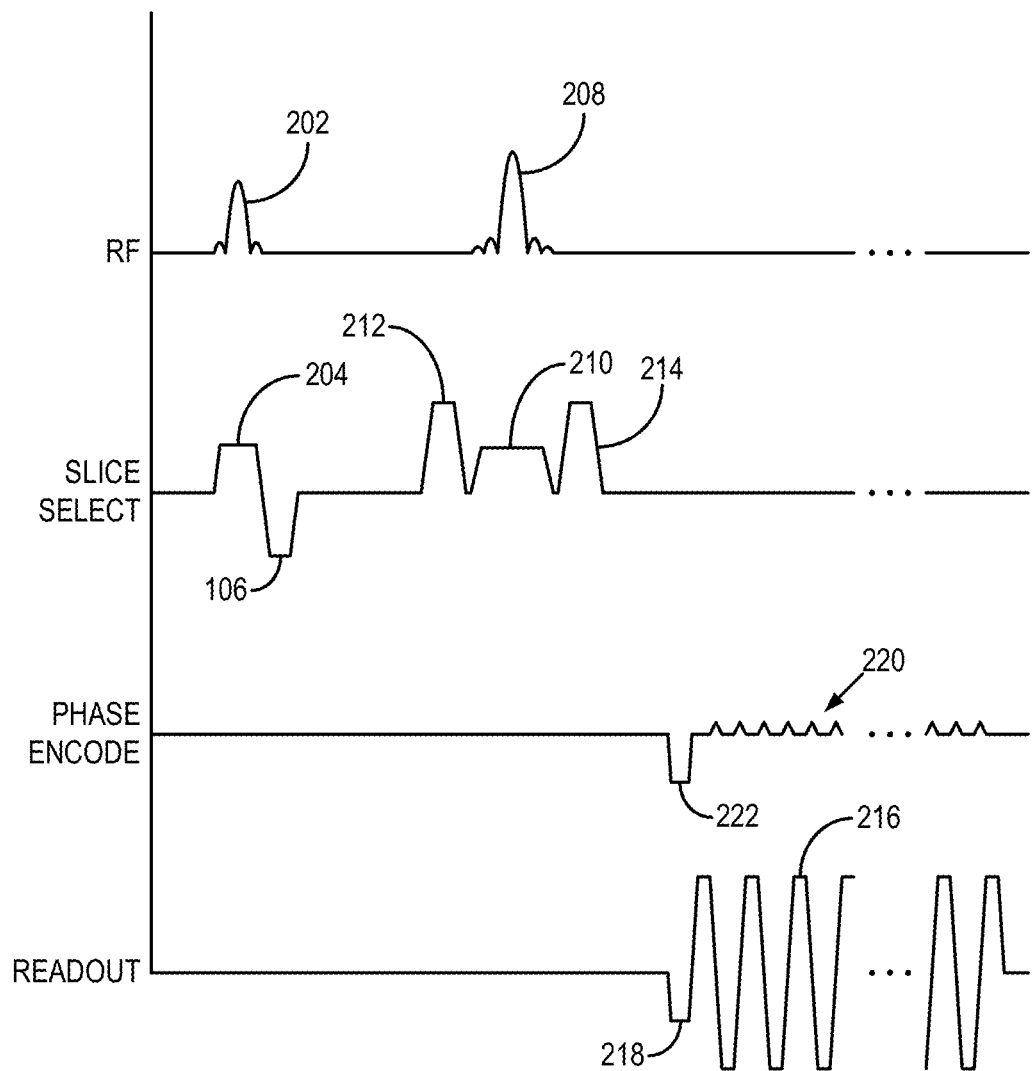
FIG. 2A is a pulse sequence diagram that can be performed by the MRI system of FIG. 1 in accordance with the present disclosure.

The MRI system 100 can be used to implement any of a variety of pulse sequences and imaging techniques. One non-limiting example of a pulse sequence is a spin-echo (SE) echo planar imaging (EPI) pulse sequence, as shown in FIG. 2A. In this example, data is acquired by forming and sampling spin echoes; however, data can also be acquired using a gradient-echo EPI sequence. The pulse sequence includes a radio frequency ("RF") excitation pulse 202 that is played out in the presence of a slice-select gradient 204 in order to produce transverse magnetization in a prescribed imaging slice. The slice-select gradient 204 includes a rephasing lobe 206 that acts to rephase unwanted phase dispersions introduced by the slice-select gradient 204, such that signal losses resultant from these phase dispersions are mitigated. Next, a refocusing RF pulse 208 is applied in the presence of another slice-select gradient 210 in order to refocus transverse spin magnetization. In order to reduce unwanted phase dispersions, a first crusher gradient 212 bridges the slice-select gradient 210 with a second crusher gradient 214.

Following excitation of the nuclear spins in the prescribed imaging slice, data are acquired by sampling a series of gradient echo signals in the presence of an alternating readout gradient 216. The alternating readout gradient is preceded by the application of a pre-winding gradient 218 that acts to move the first sampling point along the frequency-encoding, or readout, direction by a prescribed distance in k-space. Spatial encoding of the echo signals along a phase-encoding direction is performed by a series of phase encoding gradient "blips" 220, which are each played out in between the successive signal readouts such that each echo signal is separately phase-encoded. The phase-encoding gradient blips 220 are preceded by the application of a pre-winding gradient 222 that acts to move the first sampling point along the phase-encoding direction by a prescribed distance in k-space. The pulse sequence can be repeated a plurality of times while applying a different slice-select gradients 204 and 210 during each repetition such that a plurality of slice locations is sampled.

As described above, the alternating EPI readout gradient 216, along with eddy currents, imperfect gradients, and timing errors can cause inconsistencies between k-space lines of opposite polarity (RO+/RO−), which manifest as Nyquist, or N/2, ghosts. Thus, Nyquist ghosts arise due to differences between k-space lines with positive and negative polarity. The phase difference is often modeled in x-k hybrid space as a 1st order polynomial given by $$\delta = \frac{\pi \kappa}{N_x} x + \phi,$$

where x refers to the discrete position in the RO dimension of the spatial domain, $\phi$ is a spatially constant phase shift between the RO+ and RO− lines, $\kappa$ characterizes the slope ($\kappa=1$ corresponds to a one pixel shift between RO+ and RO− in k-space), and $N_x$ is the number of RO points. According to the Fourier shift theorem, the measured image can be described as:

$$I_{meas}(x,y) = I_0(x,y)\cos\left(\frac{\pi \kappa x}{N_x} + \phi\right) + iI'_0(x,y)\sin\left(\frac{\pi \kappa x}{N_x} + \phi\right) + \varepsilon(x,y); \quad \text{Eqn. 3}$$

where $I_0(x,y)$ is the ideal, ghost-free image in the readout (RO) and phase encoding (PE) directions, respectively, and $\varepsilon(x,y)$ is random thermal noise. The prime operator, ', indicates a shift in the image domain such that $$I'_0(x,y) = I_0\left(x, y \pm \frac{FOV}{2}\right).$$

In the case of multi-shot or PE-undersampled acquisitions, equation 3 becomes less straightforward. The reconstructed image will contain multiple replicas of the objects (ghosts) at locations given by $$I'_0(x,y) = \sum_{j=0}^{N_{seg}R-1} I_0\left(x, y \pm \frac{(2j+1)FOV}{2N_{seg}R}\right),$$

where $N_{seg}$ is the number of segments and R is the PE-undersampling factor. The ghosts will have an additional spatially-dependent signal modulation that varies with $N_{seg}$ and sensitivity profiles. For example, for an acquisition with R=3 undersampling, the ghost will appear shifted by ⅙ FOV, ⅜ FOV, and ⅝ FOV relative to the object.

As described above, Nyquist ghosts are commonly corrected using a three-line navigator (referred to hereinafter as "Method A") through $k_y=0$ with polarity RO+/RO−/RO+. The linear phase difference between the positive and negative lines (δ) is fit in hybrid space to determine the correction parameters $\kappa$ and $\phi$.

Figure 2B:
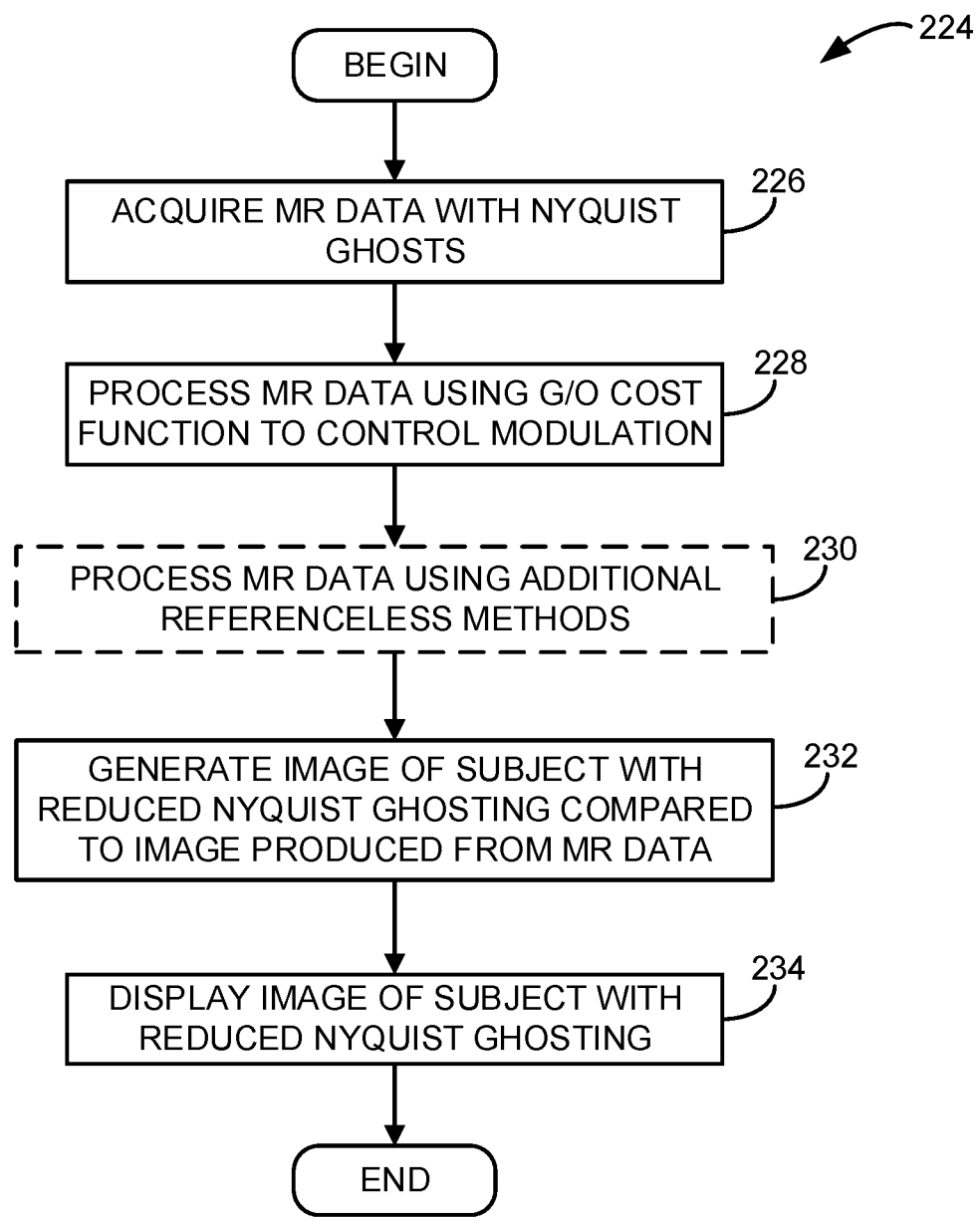
FIG. 2B is a flow chart setting forth some non-limiting examples of steps in a method in accordance with the present disclosure.
Figure 3A:
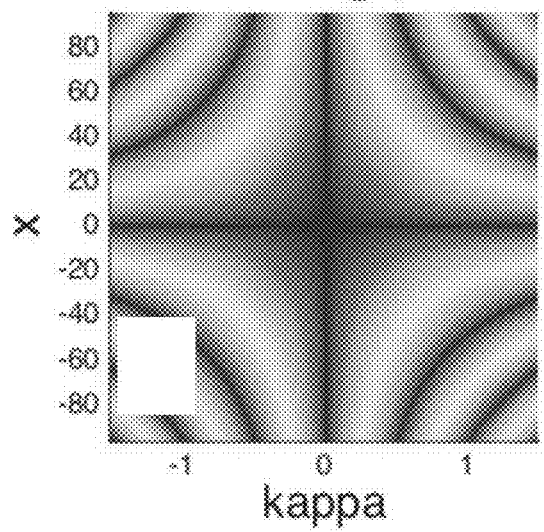
FIG. 3A is a graph showing the G/O cost function for values of x and indicating that, as kappa goes to 0, the G/O cost function is minimized.
Figure 3C:
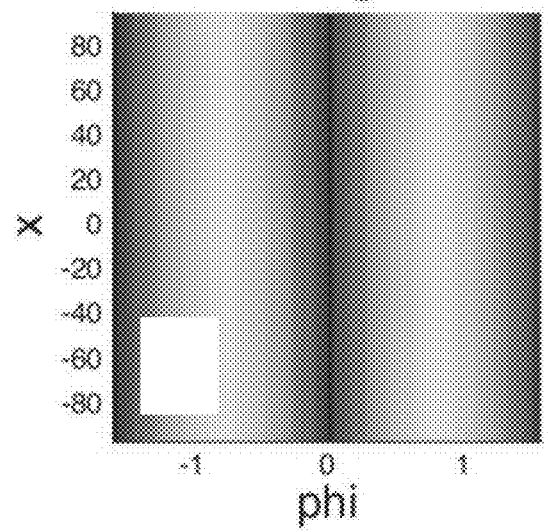
FIG. 3C shows that, assuming kappa is 0, phi can be readily chosen for any given x.
Figure 3B:
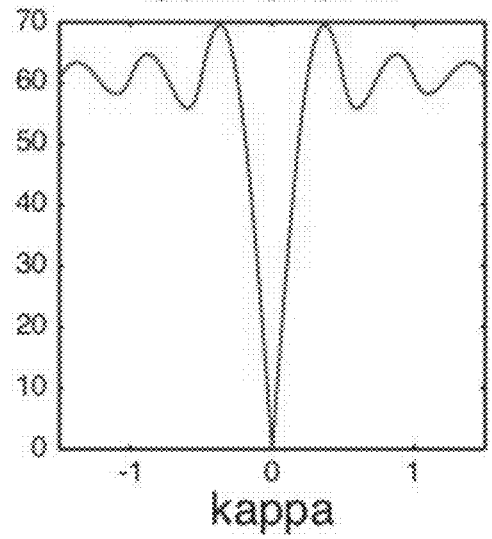
FIG. 3B is a graph showing the G/O cost function and indicating that the sum over x is also minimized as kappa approaches 0.
Figure 3D:
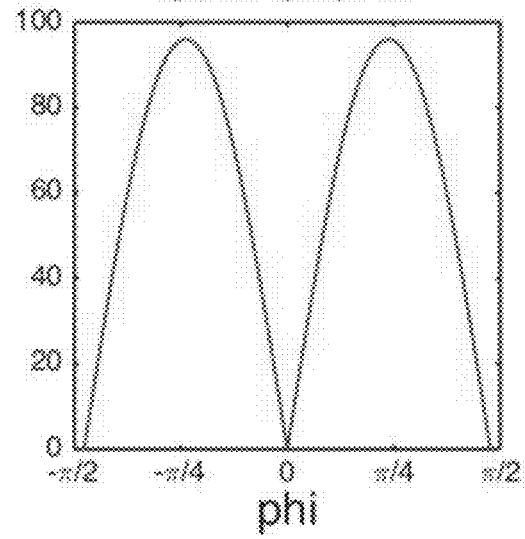
FIG. 3D shows that, assuming kappa is 0, the sum over x is minimized as phi goes to 0.

On the other hand, the present disclosure provides a referenceless method that can be applied as a first order correction by estimating $\phi$ and $\kappa$ solutions that minimize the cost function $f_{cost}(\phi, \kappa)$. Referring to FIG. 2B, one non-limiting example of some steps of a process 224 in accordance with the present disclosure is provided. The process 224 may include acquiring MR data that includes Nyquist ghosts. This data may be acquired anew using an MR system, such as described above with respect to FIG. 1, else it may include accessing previously-acquired, stored MR data, if desirable data has been stored.

At process block 228 the MR data is processed using a cost function to control modulations within the data. More particularly, the MR data may be processed using the cost function ($\phi, \kappa$) that exploits a cosine and sine modulation in a ghosted image component of the data, which may be referred to as a Ghost/Object minimization.

Specifically, the cost function for the Ghost/Object minimization (hereinafter referred to as "G/O" or "Method D") of the present disclosure can be calculated by taking the ratio of the magnitude of the measured image over a shifted copy, applying a 2D median filter for denoising, and summing over all pixels in the image domain as follows:

$$f_{cost}^{-1} = \sum_{x,y} F_{med2D}\left(\frac{|I_{meas}(x, y)|}{|I'_{meas}(x, y)|}\right); \qquad \text{Eqn. 4}$$

where $F_{med2D}$ refers to a 2D median filter applied to reduce image noise and the shift in $I'_{meas}(x,y)$ aligns the object with the expected location(s) of the ghost(s) as described above. For practical purposes, $I'_{meas}(x, y)$ is restricted to the sum over $j=0$ to $j=N_{seg}R-1$, which corresponds to the higher intensity ghosts located closest to the object.

The summation is taken over the entire image and does not require selection of the object or ghost regions, however, any pixels in $I'_{meas}(x, y)$ with very low noise values may bias the cost function by adding an overly large value to the summation. Therefore, the 2D median filter, $F_{med2D}$, is applied to remove these outlier values.

Although the exact value of the cost function will depend on the image, it can be shown numerically that the region of the image containing the object without any overlapping Nyquist ghost dominates the cost function when κ and ϕ are near the correct solution. Because of the sine and cosine modulation of the signal intensity in the ghost and object (equation 3), the inverse cost function can be approximated as $$f_{cost}^{-1} \approx \sum_{x, y_{object}} \left|\cot\left(\frac{2\pi\kappa x}{N_x} + \phi\right)\right|,$$

where the sum is taken over the region of the measured image that contains only pure object and the noise is considered negligible. Put another way, it is clear that $f_{cost}^{-1}$ cost approaches ∞ when ϕ=κ=0. Therefore, $f_{cost}$ is minimized in the ghost-free image.

Returning to FIG. 2B, the above-described processing of the MR data using the G/O cost function, $f_{cost}$, designed to create a ghost-free image may be, optionally, combined with other referencesless methods at process block 230. As some non-limiting example, some referenceless methods may include:
 "Entropy" (hereinafter referred to as "Method B") refers to the image entropy in the spatial domain, measured using Matlab's (Mathworks, Natick, Mass.) "entropy" function.
 "SVD" (hereinafter referred to as "Method C") refers to a k-space reorganized into GRAPPA-like kernels before performing singular value decomposition and summing over the tail of the singular values.
 "Ghost/Object minimization" (hereinafter referred to as "Method D") refers to a ghost correction (G/O), which is described hereafter.
 "Median" (Method E) refers to the median of the (ϕ, κ) values from Methods B, C, and D. Alternatively, the mean of the (ϕ, κ) values from Methods B, C, and D or other constructs may be used.

Thus, if included at process block 230, the process 224 can be changed from Method D to Method E or a variation thereon. For example, a discrete search may be performed to select an estimated κ and ϕ. Then, an iterative process may be used to get a more precise value of κ and ϕ. As another example, GRAPPA unaliasing can be incorporated. In this case, process block 226 includes acquiring the MR data using an accelerated, parallel imaging acquisition and process block 228 includes processing the acquired MR data using GRAPPA unaliasing before processing the MR data with the G/O cost function. In yet another example, SMS unaliasing can be incorporated. In this case, process block 226 includes an SMS acquisition and process block 228 is performed on the combined slices of the multi-band data, followed by an SMS/MB unaliasing. Thereafter, the process iterates to again process the MR data, this time as separate slices, using the G/O cost function.

Whether or not the MR data process at process block 228 using G/O cost function is combined with other referenceless methods at process block 232, the above process may be implemented in an iterative process or may be a single pass. Finally, an image of the subject is produced at process block 232 with reduced Nyquist ghosting compared to an image produced from the MR data prior to processing using the G/O cost function. Finally, at process block 234, the image with reduced Nyquist ghosting may be displayed, for example, using any of the displays described above with respect to FIG. 1.

As explained above, the exact value of the cost function will depend on the geometry of the object, which will determine the amount of overlap between the ghost and the object in the PE FOV. However, to gain some intuition about how it works, the cost function can be analytically shown to be minimized in a ghost-free image for the special case in which 1) k-space is fully sampled in one shot ($N_{seg}=R=1$), 2) the object occupies less than ½ the FOV so that the ghost and object do not overlap, and 3) the ghost consists of a single term, either linear (κ) or constant (ϕ). While this situation can be understood to be impractical, it provides an illustration of the systems and methods provided herein. Additionally, as described below, a simulation of a Shepp-Logan phantom can be used to demonstrate that there is also a local minimum at κ=0 and ϕ=0 in the more realistic case where the ghost and object overlap and the ghost consists both a linear and constant term and PE undersampling is used.

In this simplified case the cost function defined above can be written as:

$$f_{cost}^{-1} = \sum_{x,y} F_{med2D}\left(\frac{|I_{meas}(x, y)|}{|I'_{meas}(x, y)|}\right) = \qquad \text{Eqn. 5}$$

$$\sum_{x}\sum_{y} F_{med2D}\left(\frac{|I_{meas}(x, y)|}{\left|I_{meas}\left(x, y - \frac{FOV}{2}\right)\right|}\right).$$

Now consider sections of the image in the y direction where 0<y<a=ghost, a<y<b=noise (ε(x, y)), b<y<c=object, c<y<d=noise (ε(x, y)), and d<y<FOV=ghost. Due to the sine and cosine modulation in the object and ghost, respectively, the sum can be broken down to:

$$f_{cost}^{-1} = \sum_{x}\left(\sum_{y=0}^{a} \frac{I(x, y)\cos(2\pi\kappa x + \phi)}{I(x, y)\sin(2\pi\kappa x + \phi)} + \right. \qquad \text{Eqn. 6}$$

-continued $$\sum_{y=b}^{c} \frac{I(x,y)\sin(2\pi\kappa x+\phi)}{I(x,y)\cos(2\pi\kappa x+\phi)} + \sum_{y=d}^{FOV} \frac{I(x,y)\cos(2\pi\kappa x+\phi)}{I(x,y)\sin(2\pi\kappa x+\phi)} \Bigg)$$

Notice how $I_{meas}=I$ for simplicity, and the noise will be considered negligible, allowing $F_{med2D}$ to be ignored and $\Sigma_{y=a}^{b}\varepsilon(x,y)=\Sigma_{y=c}^{d}\varepsilon(x,y)=0$.

Equation (6) can be simplified as:

$$f_{cost}^{-1}=\Sigma_x C(\cot(2\pi\kappa x+\phi)+\tan(2\pi\kappa x+\phi)) \qquad \text{Eqn. (7)}.$$

where C is a constant that defines the length of the object in y, such that $C=a+c-b+FOV-d$. Finally, for small values of $\kappa$ and $\phi$, $\cot(2\pi\kappa x+\phi)\gg\tan(2\pi\kappa x+\phi)$ and therefore $f_{cost}^{-1}\approx\Sigma_x \cot(2\pi\kappa x+\phi)$, which is minimized in the ghost free image (i.e. $\kappa=\phi=0$).

This can be shown graphically as well in FIG. 3. For simplicity, first consider the case where $\phi=0$ and choose a reasonable range for x and $\kappa$, $-96<x<96$ and $-1.5<\kappa<1.5$. It can be seen in FIG. 3A that $\kappa=0$ minimizes the Ghost/Object for all values of x. Thus, the sum over x is also minimized at $\kappa=0$, as shown in FIG. 3B. Next, consider the case in which $\kappa=0$ and choose $-96<x<96$ and $-\pi/2<\phi<\pi/2$. Again, for all values of x, $\phi=0$ minimizes the Ghost/Object, as seen in FIGS. 3C-D.

Though not illustrated here, a simple phantom case can be used to demonstrate that the Ghost/Object is minimized at $\kappa=\phi=0$ for various degrees of ghost/object overlap and PE undersampling. Note that the ghost in this demonstration can contain both linear and constant terms. The varying degrees of overlap between the ghost and object in a modified Shepp-Logan phantom can be used with varying degrees of ghosting. A linear ghost can be added to each ideal phantom for $\kappa$ from −2 to 2 in steps of 0.1 and $\phi$ from −0.5 to 0.5 in steps of 0.02. In this study, the Ghost/Object cost function was again minimized in the ideal case where both $\kappa=0$ and $\phi=0$. Similarly, the Ghost/Object cost function was minimized at $\kappa=\phi=0$ for varying degrees of undersampling from R=1 to R=4. In this case the FOV shift was determined based on the undersampling factor as: shift=FOV/(2*R); for example, for R=3 a ⅙ FOV shift is used.

One of the advantages of the method using Ghost/Object minimization is that it does not require a separate reference scan. Also, the method Ghost/Object minimization is more robust in the presence of off-resonance signals. Furthermore, compared to the standard navigator, the method yields lower mean and variance in ghost level. Further still, the method using Ghost/Object minimization improves single referenceless methods via natural combination of all (entropy, SVD, and G/O) by reducing the effect of a failure by any single method.

To simulate the effect of varying noise, a synthetic image was generated in Matlab (modified Shepp-Logan) and modified with a linear ghost artifact prior to adding noise. One hundred different phase values were randomly selected, with parameters in practical ranges ($[-1.5<\kappa<1.5]$ and $[-0.3<\phi<0.3]$), and Gaussian, complex noise was added to linearly sample 25 different SNR levels for each set of ghost parameters, where SNR=SNR=$\langle S_{max}\rangle/0.66*\sigma_{noise}$, $\langle S_{max}\rangle$ is the mean image intensity in the region of maximum signal (the phantom rim), and $\sigma_{noise}$ is the standard deviation of the noise magnitude. The cost functions can be calculated on the noisy data for Entropy, SVD, and G/O over a multi-resolution discrete search space.

In one non-limiting example, this was done and the solutions for each minimization were used to correct the simulated ghost on the noise-free data and the RMS error was measured between the ideal and ghost-corrected images and averaged over all 100 trials for each noise level, as indicated in FIG. 4A-4D. Notably, in FIG. 4D, the boxes indicate the regions used to measure the average noise level in root sum of squares images.

To acquire clinical data, single-shot 2D SE-EPI DWI was acquired under IRB-approved protocols from 41 female subjects including 15 clinical patients undergoing breast cancer screening (age min/med/max=40/52/68), 13 patients with biopsy-proven cancer receiving MRI for treatment monitoring (28/47/72), and 13 healthy volunteers (18/21/66). Four subjects undergoing screening had silicone implants in one or both breasts. All subjects were positioned headfirst prone in a Siemens Prisma$^{fit}$ 3T scanner using a 16-channel Sentinelle breast coil. Diffusion images were acquired following the protocol used in the clinical trial ACRIN 6698, with TR=8000 ms and TE 51 ms for monopolar diffusion (12 participants) or 74 ms for bipolar diffusion (29 participants), 36-50 4 mm axial slices with 320×320 mm in-plane FOV at 1.7×1.7 mm resolution, right-left phase encoding, in-plane undersampling of R=3, 6/8 partial Fourier, SPAIR fat suppression, and total acquisition time ~5 minutes. One of the following three diffusion schemes was used to sample three orthogonal diffusion directions for each subject: b=0, 100, 600, and 800 s/mm2 (5, 9, 9, 9 averages=32 volumes) [21 participants]; b=0, 100, 600, and 800 s/mm2 (4, 6, 6, 6 averages=22 volumes) [5 participants]; b=0, 100, and 800 s/mm2 (5, 9, 9 averages=23 volumes) [15 participants]. A 3-line navigator was acquired with phase encoding disabled for each coil, slice, and b-value/diffusion direction and for both the autocalibration scan (ACS lines) and undersampled data. T1-weighted anatomical images were acquired using a 3D VIBE sequence (RF-spoiled, 3D gradient echo) with fat suppression.

With the data in hand, both ACS lines and undersampled data were reconstructed off-line with per-acquisition, per-coil, and per-slice ghost correction, followed by GRAPPA unaliasing. For the 3-line navigator correction (Method A), the phase difference between the center line and average of the 1st and 3rd lines of each navigator was smoothed with a Savitzkey-Golay filter (sgolay, Matlab), weighted by the signal intensity to the fourth power, and fit to a first-order polynomial in x–$k_y$ hybrid space.

The referenceless methods were applied to the low-resolution ACS lines using a multi-resolution discrete search centered at $\phi=0$ and $\kappa=0.6$ in Matlab to determine $\phi_{ACS}$ and $\kappa_{ACS}$. The corrected ACS lines were used to calculate the GRAPPA weights. Thus, the G/O method can be used to improve the auto-calibration signal (ACS), which may improve downstream GRAPPA reconstruction. $\phi_{ACS}$ and $\kappa_{ACS}$ were also applied as an initial correction for the undersampled diffusion-weighted data. To refine $\phi$ and $\kappa$, a second iteration was performed using a non-linear minimization (fminsearch) including GRAPPA unaliasing in each step: i.e. a candidate ($\phi$, $\kappa$) correction was performed on each channel of the undersampled data before GRAPPA unaliasing so the cost function could be evaluated on the unaliased reconstructed image. As discussed above, these referenceless methods can be used with undersampled data either iteratively or non-iteratively, depending on the geometry and aliasing factor.

Method D (Median) included a combination of the four referenceless methods by taking the median of $\phi$ and $\kappa$ from each method to reconstruct both ACS and undersampled data.

Assuming a monoexponential decay diffusion model, ADC maps were generated using a pixel-by-pixel linear fit of the natural log of the signal intensity across b-values.

Due to the N/2 nature of Nyquist ghosts, R=3 undersampling, and symmetric anatomy of axial breasts images, a large portion of the residual ghosts fell along the midline between the right and left breasts, as illustrated in FIGS. 4A-4D. Thus, the signal level of the background region was used as a surrogate measurement of the ghost level in the full image. To measure the signal in the background region, the T1-weighted anatomical image was resampled to match the DWI image matrix, thresholded, and dilated to automatically create a mask of object and background. All area posterior to the chest wall was automatically classified as object. We also measured the noise level for each case based on the average signal intensity of noise-only corner regions of the volume as shown in FIGS. 4A-4D. We defined the ghost intensity for each method, acquisition, and subject over the whole volume as the average signal in the background region compared to the average noise level.

To compare the ghost correction performance, the whole-volume ghost measurements were averaged for each subject across averages at each b-value, and then a linear mixed model was applied with ghost correction method, b-value, and their interaction as covariates, adjusting for body mass index (BMI). A pairwise comparison was made between each correction method based on the model-estimated ghost intensity. To control type I error for multiple comparisons, Bonferroni correction was applied, and a two-sided p-value<0.005 (0.05/10) was considered statistically significant for pairwise comparisons among five methods. The ghost intensity estimates were also compared between methods on a per-b-value basis in a pairwise way. Statistical significance was set to P<0.00125 (0.05/40) based on Bonferroni correction. SAS system (version 9.4; SAS Institute, Cary, N.C.) was used in all statistical analyses.

Figure 5:
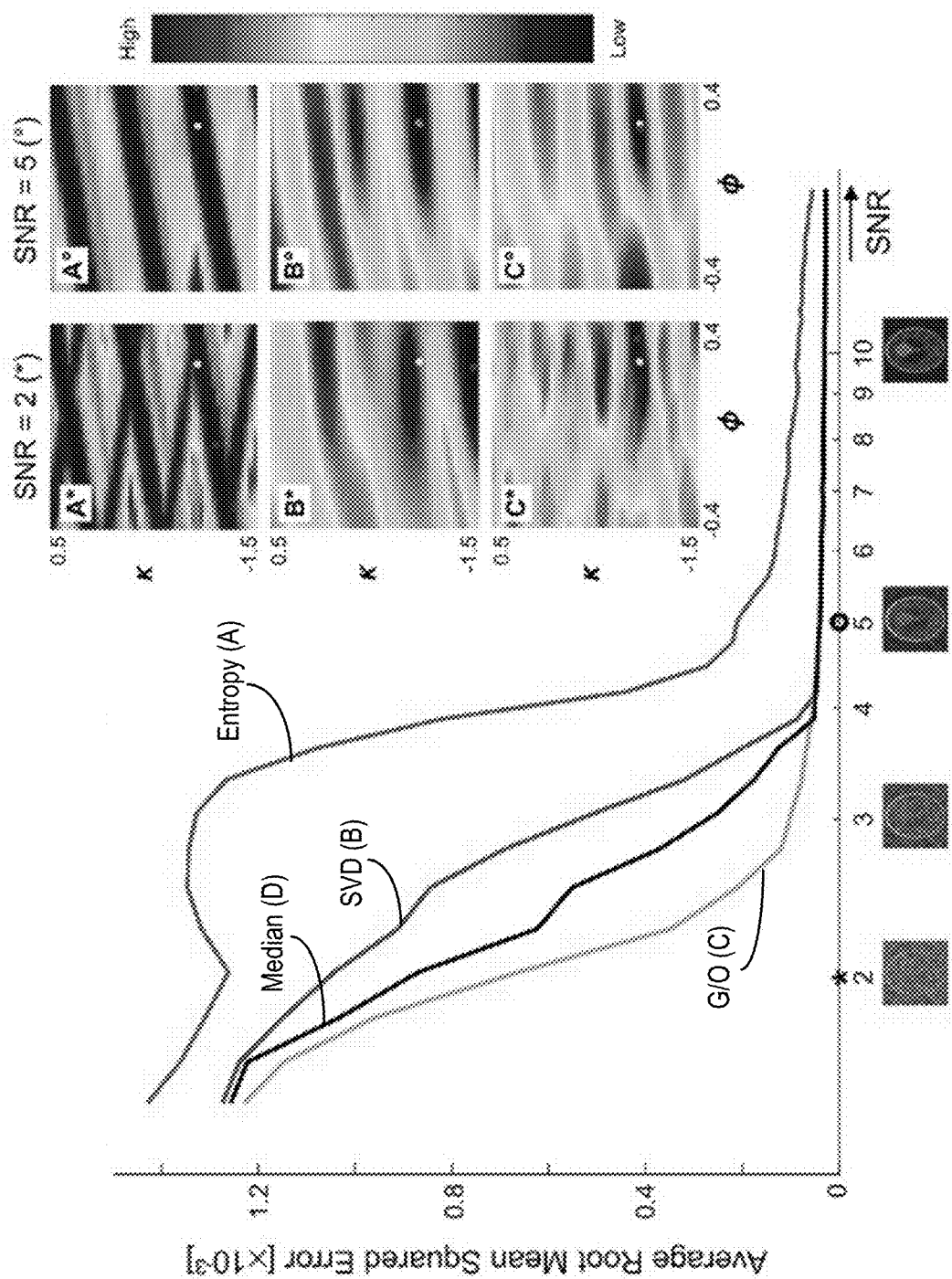
FIG. 5 is a graph of a simulation of noise effect on cost functions. This plot shows the accuracy of each method, averaged over 100 trials, for increasing SNR levels. Example images are shown for 4 (of 25 tested) sample SNR values. Inset plots show the cost functions for a single trial at two SNR levels, indicated on the x-axis by * and °. With decreasing SNR, additional local minima develop and minimum regions spread out. White and red circles indicate the correct and estimated ghost parameters, respectively.

FIG. 5 illustrates the performance of the referenceless methods with increasing levels of SNR. While the error increases at lower levels of SNR for all four methods, entropy is most sensitive to noise, followed by SVD, Median, and finally G/O. This sensitivity is reflected in the shape of the cost functions illustrated in the corresponding inset plots of FIG. 5 that show the cost functions for a single trial at two SNR levels, indicated on the x-axis by * and °.

As SNR decreases, the minimum regions spread out and additional local minima develop that do not correspond to the ghost-free image, especially for Entropy and SVD. While all three referenceless cost functions have clear global minima at low noise levels, the cost functions vary in shape, especially as the noise level increases, suggesting that they each contain some unique information.

Figure 6:
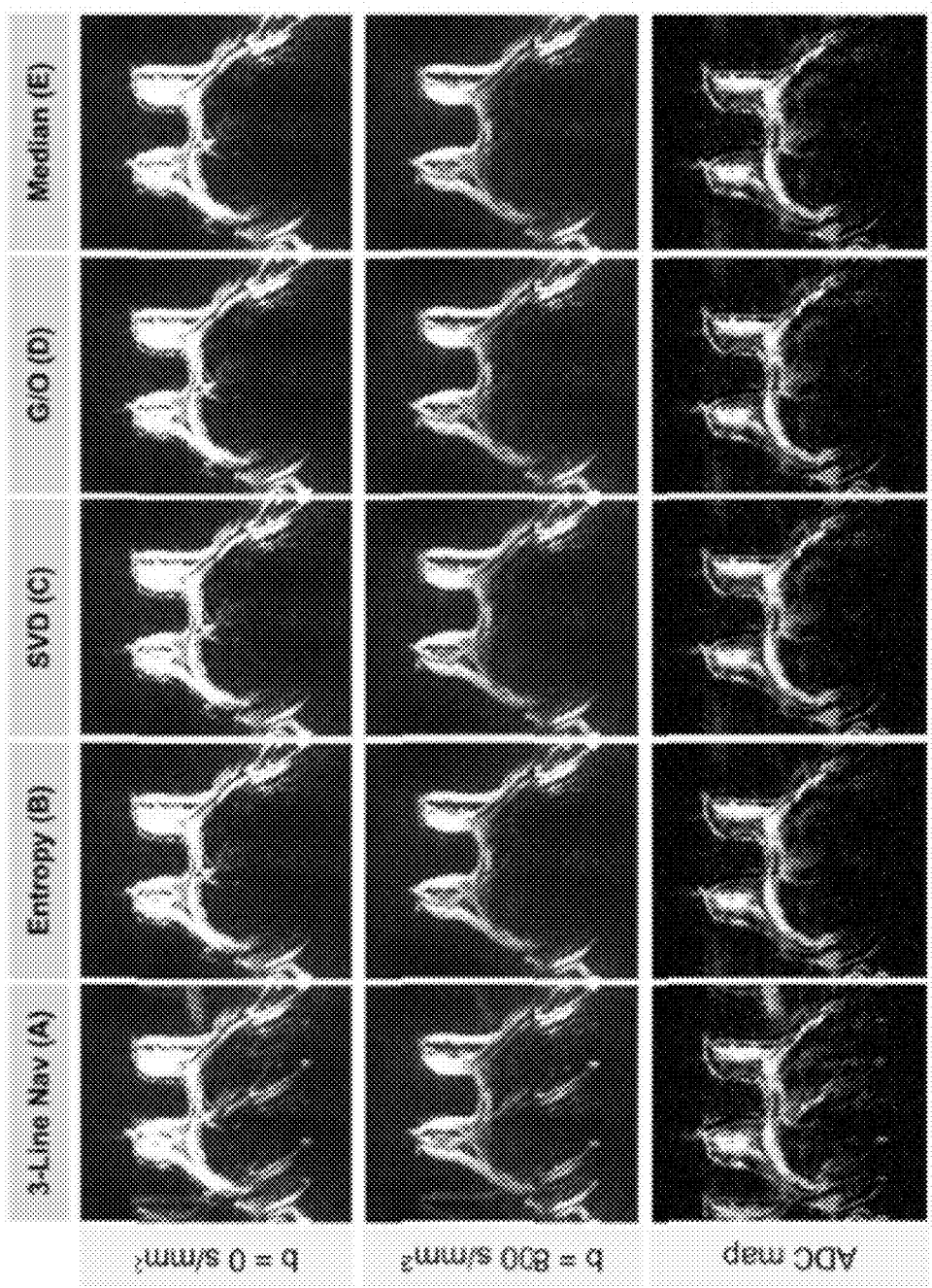
FIG. 6 is an array of correlated images of single-slice DWI from two example cases. A single acquisition of b=0 and 800 s/mm2 images and an ADC map are shown. The example is chosen as a representative case in which the referenceless methods outperform the 3-line navigator. Scaled to highlight Nyquist ghosts.

The performance of all five ghost correction methods varied across cases and slices. The 3-line navigator tended to fail more frequently than the referenceless methods in the 41 breast cases tested. An example is shown in FIG. 6 that represents a typical case where the 3-line navigator failed and the referenceless methods significantly reduced the ghost at both b=0 and b=800 s/mm2, as well as the resulting ADC map.

Figure 7:
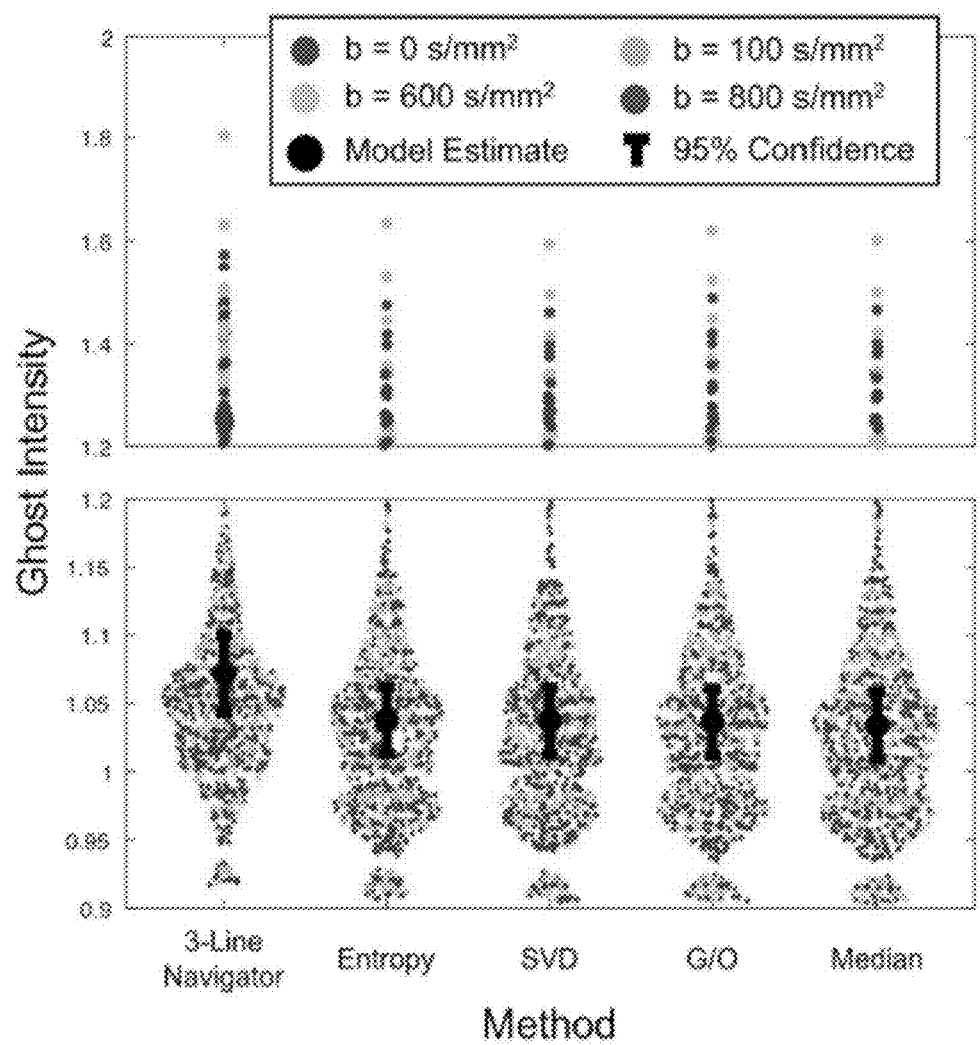
FIG. 7 is a set of correlated graphs of whole-volume ghost intensity plotted over the method used to acquire/process each set of data. Colored points indicate ghost intensity measured over the volume of each subject and acquisition; color indicates b-value. The black circles indicate the ghost intensities estimated according to the adjusted linear mixed model with 95% confidence intervals.

The overall effects of ghost correction method are shown in FIG. 7, which plots the ghost intensities measured over the whole volume for each subject and acquisition. The mean ghost levels estimated according to the adjusted linear mixed model are overlayed including 95% confidence intervals. All four referenceless methods generally reduce ghost levels compared to the standard approach. According to the adjusted linear mixed model, the performance of all four referenceless methods (B-E) is statistically superior (p≤0.0002) to the standard linear correction (A). While there is no statistical difference between the performance of the entropy, SVD, and G/O referenceless methods (B-D), the median combination of referenceless methods (E) is estimated to significantly outperform any single referenceless method alone (p<0.0001).

Figure 8:
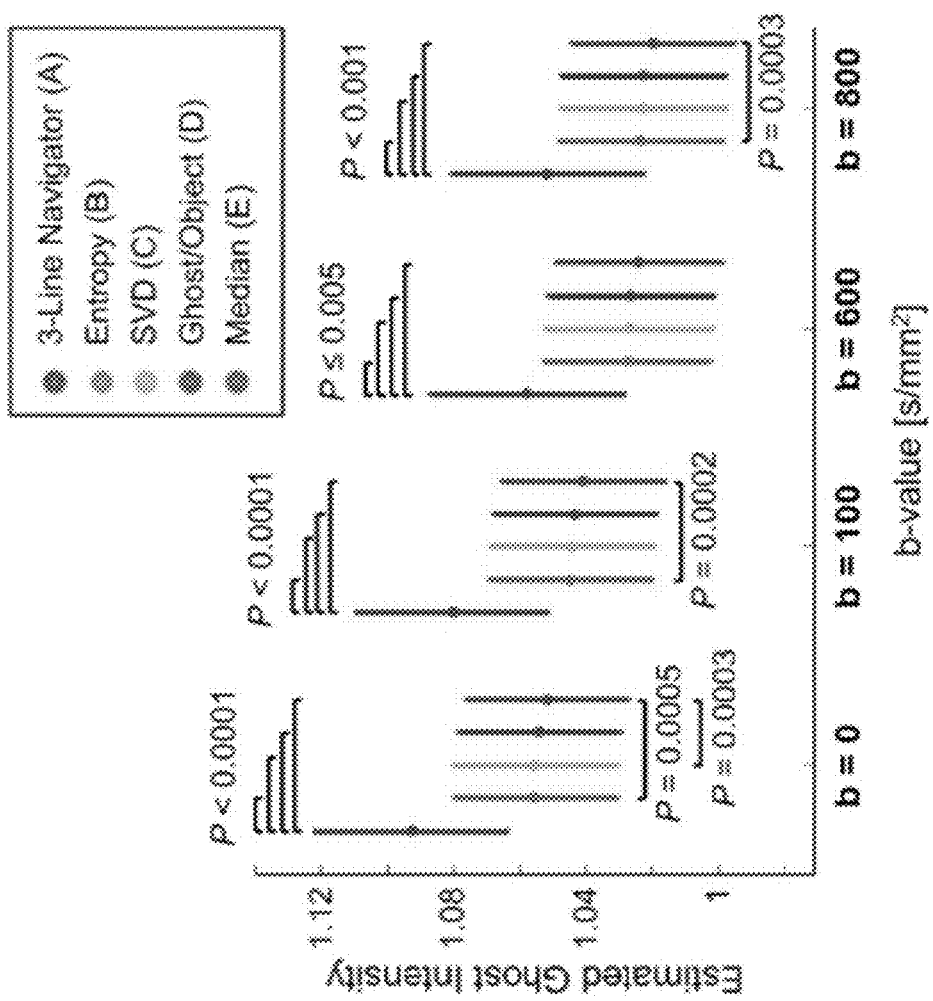
FIG. 8 is a set of graphs of ghost intensity by method and b-value. Ghost intensity and its 95% confidence interval estimated by the linear mixed model given b-value and ghost correction method. Threshold for statistical significance is set to P<0.00125 based on Bonferroni's method for multiple comparisons.

The mean ghost intensities for each method separated by b-value according to the full linear mixed model are plotted in FIG. 8; p-values less than 0.00125 are indicated. The mean ghost intensity of all referenceless methods (B-E) is lower than that of the standard 3-line navigator at all four b-values (P<0.001). The differences between entropy, SVD, and G/O referenceless methods are not statistically significant regardless of b-value. The median method (E) yields the lowest ghost intensity value at all four b-values, however, E only outperforms B-C with statistical significance compared to Entropy and SVD at b=0 s/mm2 and to Entropy at b=100 and 800 s/mm$^2$.

While the 3-line navigator is acquired before diffusion weighting and is therefore independent of b-value, the referenceless methods depend on the diffusion-weighted data, making them potentially more sensitive to the signal loss at high b-values. However, we have shown here that all four referenceless methods outperform the 3-line navigator at all four b-values up to b=800 s/mm$^2$.

All five ghost correction methods estimated and applied two linear parameters on a per-coil, per-slice, and per-acquisition basis. In a small number of cases none of the ghost correction methods fully suppress the ghost, suggesting that it may be necessary to use some non-linear or time-varying correction. The referenceless methods may be extended to include higher-order parameters or correction that varies over the RO train if the necessary correction can be modeled by a small number of parameters. However, the computational time will quickly grow as the model increases in complexity.

The referenceless methods represent a data-driven approach to correct Nyquist ghosts. They can be applied retrospectively to a wide variety of data acquisitions without the need for any additional reference scan as methods like phase labeling for additional coordinate encoding (PLACE) and phase mapping require. Ghost correction by referenceless methods also does not rely on coil-sensitivity profiles, as methods like phase array ghost elimination (PAGE) do, and therefore preserve all information about coil-sensitivity for the purpose of maximizing acceleration. Additionally, by removing the three-line navigator, it may be possible to shorten the TE, for example, in monopolar diffusion schemes.

SVD is the slowest referenceless method that was investigated; a full static SVD reconstruction took ~1.3 times longer than the 3-line navigator correction and further increases to ~100 (G/O) to 300 (SVD) times when the iterative approach, which includes GRAPPA unaliasing in the cost function minimization, was used to determine dynamic corrections. It should be possible to reduce computation requirements to clinically practical times with further optimization of the processing.

While the summation in equation 4 is performed over the entire image, the cost function is dominated by the object-only region because of the sine and cosine signal modulation. Although the method does not explicitly select regions of interest, it could be limited by the amount of object/ghost overlap if the object lacks signal variation in the PE direction, which would flatten the shape of $f_{cost}(\phi,\kappa)$. Additionally, G/O relies upon the removal of outlier values before taking the summation, which is not necessary for entropy or SVD. These outliers can be readily removed by applying a 2D median filter, which also produces some denoising in $f_{cost}(\phi,\kappa)$. Although this filtering does add a small bias to the comparison of the referenceless methods, median filtering did not improve the entropy metric in experiments and cannot be used with SVD as it requires complex data. However, all of the methods used, including the 3-line navigator, may be further optimized using other denoising techniques (e.g., Gaussian) and additional tuning.

Previous reports have claimed that referenceless methods performed in the image domain were limited by the amount of overlap and aliasing that arise when acceleration techniques or multi-shot acquisition are used. That is, one limitation of the referenceless methods is the increased computational requirement for optimization of the nonlinear cost functions. The systems and methods of the present disclosure can overcome the limitation of PE undersampling by incorporating the GRAPPA reconstruction in the optimization; this strategy can be used in combination with other acceleration methods as well.

The present disclosure recognizes that Nyquist ghost artifacts can modulate the true image signal and lead to errors in ADC estimation via 2 distinct mechanisms. The first is simple overlap-if any portion of a Nyquist ghost overlaps the object it can increase or decrease the object signal. Second, an incorrect phase produces a spatially varying cosine modulation of the object signal (equation 3). As provided herein, the ghost signal can be used in the image background as an estimate of the overall ghost level. Although ghost signal in the image background does not directly produce ADC errors, it is an objective measure of the overall ghost level.

Referenceless methods provide a data-based alternative to the three-line navigator for 1st-order ghost correction, which often fails in breast DWI. The present disclosure's referenceless method, Ghost/Object (G/O) minimization, which defines a cost function in the image domain that exploits the cosine and sine modulation in the ghosted image and the N/2 nature of the ghost. G/O showed lower sensitivity to noise than Entropy and SVD in a simulation at increasing noise levels. In this work, all three referenceless methods were successfully combined with accelerated imaging of R=3 and outperformed the 3-line navigator correction at all four b-values. Additionally, because each of the three cost functions employed contain some unique information, combining the referenceless methods with the median of 1st-order parameters showed a trend of improved ghost correction performance.

The above-described systems and methods have been applied to reduce residual ghosts in high-resolution breast DWI acquired with simultaneous multi-slice (SMS) SE-EPI using G/O to correct 1st order ghosts. In one non-limiting example, sixteen breast cancer patients were scanned prone on a Siemens 3T prismafit with a 16-channel breast coil (Sentinelle) under an IRB-approved protocol. DWI was acquired using 2D SE-EPI with 256 sagittal slices of 1.25 mm with SMS MB=4, which are reformatted to axial images for clinical viewing. The following parameters were used: TR/TE=6500/60.80 ms, 1.25×1.25 mm nominal in-plane resolution, head/foot PE direction, GRAPPA R=2, and monopolar diffusion (4 at b=0, 4 at b=800 s/mm2). Standard T1-weighted anatomical images were also acquired.

Two first-order ghost correction methods were applied to both the ACS data and each undersampled acquisition on a per-channel and per-slice basis. The 3-line navigator, which represents typical online correction, acquires a navigator through $k_y$=0 (RO+/RO−/RO+) to measure the phase difference. G/O minimization was performed directly on ACS and undersampled data, starting with a wide discrete search and refined with a simplex search. After SMS unaliasing, the ghost correction was adjusted in a slice-specific way, statically for the 3-line navigator (based on the difference between ACS and MB navigators) and dynamically for G/O (based on a second iteration of the minimization problem). To improve GRAPPA unaliasing performance, original ACS data was combined with RO-reversed ACS data to reduce ghosts before calculating weights.

The residual ghost levels were measured based on the signal in the background region. T1-weighted images were automatically masked and resampled onto the DWI to define the object region. The ghost signal was measured as the whole-volume background signal compared to the average signal in a noise-only volume.

In vivo b=0 and 800 s/mm2 images were produced. The 3-line navigator clearly failed, causing Nyquist ghosts and poor GRAPPA unaliasing performance. Small levels of GRAPPA errors were also present in G/O images. The artifacts in the PE direction influenced the SMS unaliasing performance and overall axial image quality. Several artifacts were present in the slice dimension after correction by 3-line navigator, which were greatly reduce by G/O. The ghost intensity of G/O was plotted versus the 3-line navigator for each acquisition. For all cases, G/O either performed equivalently or outperformed the standard 3-line navigator.

The ghost intensities were plotted separated by b-value. According to a paired t-test (N=16) there was a significant difference between the performance of G/O and the 3-line navigator at both b=0 and b=800 s/mm2.

The G/O method does not rely on any reference data and was applied directly to both R=2 undersampled data and SMS data after unaliasing, allowing for a completely dynamic and slice-specific correction. In accordance with the present disclosure, the background signal acts as a surrogate for ghost intensity. The background includes both Nyquist ghosts and GRAPPA unaliasing artifacts, which are often caused by the poor ghost correction of ACS lines. Some unaliasing artifacts were present in both G/O and 3-line navigator reconstruction. Importantly, Nyquist ghosts in the background region imply a signal change in the object and ghost that may overlap the object, biasing the ADC values. Moreover, severe ghost failures make image interpretation difficult.

The standard 3-line navigator is insufficient for ghost correction of high resolution, breast SE-EPI DWI with SMS. The G/O referenceless method provided herein provides a more reliable 1st-order ghost correction in a dynamic and slice-specific way, which improves image quality and reduces bias in ADC values compared to the standard correction.

The present invention has been described in terms of one or more preferred embodiments, and it should be appreciated that many equivalents, alternatives, variations, and modifications, aside from those expressly stated, are possible and within the scope of the invention.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The invention claimed is:

1. A system comprising:
a magnet system configured to generate a polarizing magnetic field about at least a portion of a subject;
a magnetic gradient system including a plurality of magnetic gradient coils configured to apply at least one magnetic gradient field to the polarizing magnetic field;
a radio frequency (RF) system configured to apply an RF field to the subject and to receive magnetic resonance signals from the subject using a coil array;
a computer system programmed to perform steps including:
(i) access data corresponding to the magnetic resonance signals received from the subject that includes Nyquist ghosts;
(ii) process the data to control artifacts using a cost function that exploits a cosine and sine modulation in a ghosted image component of the data; and
(iii) display an image of the subject produced from the data after processing of step (ii).

2. The system of claim 1 wherein the cost function is assessed in an image domain.

3. The system of claim 2 wherein step (ii) further comprises calculating a ratio of a magnitude of the images over a shifted copy, applying a denoising filter for denoising, and summing over all pixels in the images.

4. The system of claim 1 wherein step (ii) includes processing the data using at least one further referenceless method to produce combined image of the subject from the data after processing using the cost function and the at least one further referenceless method.

5. The system of claim 4 wherein step (ii) includes forming at least one of a mean and a median to produce the combined image.

6. The system of claim 1 wherein step (ii) includes applying a denoising filter to reduce image noise in the data.

7. The system of claim 1 wherein step (ii) includes processing an image formed from the MR data to exploit the sine and cosine modulation of signal intensity in the image formed from the MR data.

8. A system comprising:
a magnet system configured to generate a polarizing, magnetic field about at least a portion of a subject;
a magnetic gradients system including a plurality of magnetic gradient coils configured to apply at least one magnetic gradient field to the polarizing magnetic field;
a radio frequency (RF) system configured to apply an RF field to the subject and to receive magnetic resonance signals from the subject using a coil array;
a computer system programmed to perform steps including:
(i) accessing data acquired from a subject using the system that includes Nyquist ghosts;
(ii) processing the data using multiple referenceless methods to produce combined data from the multiple referenceless methods; and
(iii) displaying an image of the subject produced from the combined data after processing of step (ii).

9. The system claim 8 wherein the data is acquired using an accelerated imaging technique.

10. The system of claim 8 wherein step (ii) includes producing the combined data as a mean or a median of the multiple referenceless methods.

11. The system of claim 8 wherein step (ii) is performed in an image domain on images produced from the data.

12. The system of claim 11 wherein step (ii) further comprises using at least one referenceless method that includes calculating a ratio of a magnitude of the images over a shifted copy, applying a 2D median filter for denoising, and summing over all pixels in the images.

13. The system of claim 8 wherein at least one of the multiple referenceless methods includes using cost function to control a cosine and sine modulation in a ghosted image component of the data.

14. A system comprising:
a magnet system configured to generate a polarizing magnetic field about at least a portion of a subject;
a magnetic gradient system including a plurality of magnetic gradient coils configured to apply at least one magnetic gradient field to the polarizing magnetic field;
a radio frequency (RF) system configured to apply an RF field to the subject and to receive magnetic resonance signals from the subject using a coil array;
a computer system programmed to perform steps including:
(i) with a computer, accessing undersampled data acquired from a subject using the magnet system, magnetic gradient system, and RF system that includes Nyquist ghosts;
(ii) with a processor, processing the data using a referenceless method to reduce the Nyquist ghosts by using a cost function that exploits a cosine and sine modulation in a ghosted image component of the undersampled data; and
(iii) with a display, displaying an image of the subject produced from the undersampled data after processing of step (ii).

15. The system of claim 14 wherein step (ii) further includes processing the data using multiple referenceless methods to produce combined data from the multiple referenceless methods and step (iii) includes producing the image from the combined data.

16. The system of claim 14 wherein step (ii) further comprises calculating a ratio of a magnitude of the images over a shifted copy, applying a 2D median filter for denoising, and summing over all pixels in the images.

17. A magnetic resonance imaging (MRI) system comprising:
a magnet system configured to generate a polarizing magnetic field about at least a portion of a subject;
a magnetic gradient system including a plurality of magnetic gradient coils configured to apply at least one magnetic gradient field to the polarizing magnetic field;
a radio frequency (RF) system configured to apply an RF field to the subject and to receive magnetic resonance signals from the subject using a coil array;
a computer system programmed to:
acquire imaging data acquired from a subject that includes Nyquist ghosts, wherein the imaging data was acquired using the MRI system;
process the imaging data using a cost function to control the Nyquist ghosts in an image of the subject; and
a display configured to display the image of the subject produced from the data after processing the image data to control Nyquist ghosts.

18. The system of claim 17 wherein, to process the imaging data, the computer system is further programmed to reconstruct images from the imaging data and calculate a ratio of a magnitude of the images over a shifted copy, apply a 2D median filter for denoising, and sum over all pixels in the images to process the imaging data using the cost function.

19. The system of claim 17 wherein the computer system is further programmed to process the imaging data using at least one further referenceless method to produce combined image of the subject from the imaging data after processing using the cost function and the at least one further referenceless method.

20. The system of claim 17 wherein the cost function exploits a cosine and sine modulation in a ghosted image component of the data to control the Nyquist ghosts in the image of the subject.

* * * * *

UNITED STATES PATENT AND TRADEMARK OFFICE
CERTIFICATE OF CORRECTION

PATENT NO. : 11,009,577 B2
APPLICATION NO. : 16/430110
DATED : May 18, 2021
INVENTOR(S) : Jessica McKay et al.

Page 1 of 2

It is certified that error appears in the above-identified patent and that said Letters Patent is hereby corrected as shown below:

In the Specification

Column 5, Line 40, "q, G and q" should be --$G_x$, $G_y$ and $G_z$--.

Column 7, Line 66, "x-k" should be --$X$-$k_y$--.

Column 10, Line 50, "$\sum_{x,y}$" should be --$\sum x,y$--.

Column 10, Line 53, "$\sum_x \sum_y$" should be --$\sum_x \sum_y$--.

Column 10, Line 65, "$\sum_x \left( \sum_{y=0}^{\alpha} \right.$" should be --$\sum_x \left( \sum_{y=0}^{\alpha} \right.$--.

Column 11, Line 3, "$\sum_{y=b}^{c} \frac{I(x,y)\sin(2\pi\kappa x + \phi)}{I(x,y)\cos(2\pi\kappa x + \phi)} + \sum_{y=d}^{FOV} \frac{I(x,y)\cos(2\pi\kappa x + \phi)}{I(x,y)\sin(2\pi\kappa x + \phi)}$" should be --$\sum_{y=b}^{c} \frac{I(x,y)\sin(2\pi\kappa x + \phi)}{I(x,y)\cos(2\pi\kappa x + \phi)} + \sum_{y=d}^{FOV} \frac{I(x,y)\cos(2\pi\kappa x + \phi)}{I(x,y)\sin(2\pi\kappa x + \phi)}$--.

Column 11, Line 8, "$\Sigma_{y=a}^{b} \varepsilon(x,y) = \Sigma_{y=c}^{b} \varepsilon(x,y) = 0$" should be --$\Sigma_{y=a}^{b} \varepsilon(x,y) = \Sigma_{y=c}^{d} \varepsilon(x,y) = 0$--.

Column 11, Line 59, "⟨$S_{max}$⟩" should be --⟨|$S_{max}$|⟩--.

Column 11, Line 60, "⟨$S_{max}$⟩" should be --⟨|$S_{max}$|⟩--.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

In the Claims

Column 17, Claim 9, Line 59, "system claim" should be --system of claim--.